US007004932B2

(12) United States Patent
Szurko

(10) Patent No.: US 7,004,932 B2
(45) Date of Patent: Feb. 28, 2006

(54) OVERSPRAY COLLECTION BOOTH

(76) Inventor: Lester Szurko, 2805 Alameda Ct., Naperville, IL (US) 60564

( * ) Notice: Subject to any disclaimer, the term of this patent is extended or adjusted under 35 U.S.C. 154(b) by 0 days.

(21) Appl. No.: 10/350,751

(22) Filed: Jan. 24, 2003

(65) Prior Publication Data

US 2004/0147884 A1 Jul. 29, 2004

(51) Int. Cl.
*A61M 35/00* (2006.01)
(52) U.S. Cl. .................................... 604/289
(58) Field of Classification Search ............... 604/289, 604/290; 132/333, 320; 118/634, 326; 4/525, 4/524; 239/120, 207, 204; 601/156
See application file for complete search history.

(56) References Cited

U.S. PATENT DOCUMENTS

| | | | | |
|---|---|---|---|---|
| 3,918,641 | A | * | 11/1975 | Lehmann et al. ........... 118/620 |
| 4,294,191 | A | * | 10/1981 | Loof ........................... 118/634 |
| 4,662,309 | A | | 5/1987 | Mulder |
| 4,984,571 | A | | 1/1991 | Springer |
| 5,256,308 | A | | 10/1993 | Dulany |
| 5,277,652 | A | * | 1/1994 | Minor .......................... 454/52 |
| 5,453,301 | A | | 9/1995 | Saatweber et al. |
| 5,569,384 | A | | 10/1996 | Saatweber |
| 5,607,498 | A | | 3/1997 | Reighard |
| 5,690,995 | A | | 11/1997 | Fischli |
| 5,906,676 | A | | 5/1999 | Drummond |
| 6,071,558 | A | | 6/2000 | Shutic |
| 6,171,656 | B1 | | 1/2001 | Settles |
| 6,273,154 | B1 | * | 8/2001 | Laug ........................... 141/97 |
| 6,443,164 | B1 | * | 9/2002 | Parker et al. ............... 132/333 |
| 6,468,508 | B1 | | 10/2002 | Laughlin |
| 6,471,737 | B1 | | 10/2002 | Cole |
| 6,554,208 | B1 | * | 4/2003 | Venuto, Sr. ................. 239/207 |
| 6,681,417 | B1 | * | 1/2004 | Brunelle et al. ............... 4/597 |

* cited by examiner

*Primary Examiner*—Pedro Philogene
(74) *Attorney, Agent, or Firm*—Meroni & Meroni, P.C.; Charles F. Meroni, Jr.; Christopher J. Scott

(57) ABSTRACT

A booth for the collection of tanning fluid overspray comprising a booth and a collection system. The booth is sized and shaped to enclose a person having a first side wall and a second side wall, the booth having an open portion sized and shaped for ingress and egress by a person. A plurality of vent apertures are spaced within the first side wall and the second side wall to provide effective collection of airborne particles within the booth. A plurality of venting conduit lines having a plurality of venting connections connected to the vent apertures is connected to a common collection line. A suction means connected to the common collection line provides suction within the venting conduit lines, the suction drawing airborne particles within the booth through the vent apertures, venting connections and the venting conduit lines. The suction means draws the airborne particles within the venting conduit lines into a collection means. The collection means contains water for dissolving water soluble airborne particles within the air drawn from the venting conduit lines.

19 Claims, 8 Drawing Sheets

OVERSPRAY COLLECTION BOOTH

BACKGROUND OF THE INVENTION

1. Field of the Invention

The claimed invention generally relates to overspray collection booths. More specifically, the claimed invention relates to an Overspray Collection Booth designed for the collection of tanning fluid overspray during the application of tanning fluid to the human body.

2. Description of the Prior Art

People typically find sun-tanned skin attractive and have sent long periods of time exposing their skin to the sun in order to tan their skin. However, over the last several decades people have become more aware of the harmful effects of prolonged exposure to the sun and have been seeking different ways of obtaining the look of sun-tanned skin while avoiding prolonged exposure to the sun. One of the ways people have found to obtain the look of sun-tanned skin without excessive exposure to the sun is by applying tanning fluid to the skin that presents the look of sun-tanned skin.

One of the more popular ways of applying the tanning fluid is to airbrush the tanning fluid on the skin. However, during the application of the tanning fluid with an airbrush, tanning fluid tends to ricochet off of the persons body, tending to create a mess in the area around the person. It has come to my attention that there is a need for a way to collect tanning fluid overspray that occurs during the application of tanning fluid by way of an airbrush. There are several collection type devices in the prior art that have been designed for the collection of paint and paint type products, but they do not address several of the needs that are specific to the collection of tanning fluid when tanning fluid is dispensed by way of an airbrush. Several of these devices are discussed here.

U.S. Pat. No. 4,662,309 issued to Milder discloses a self-contained, compact and portable powder spray booth and powder recovery system includes a base unit, and a separate booth removably mounted upon the base unit which can be easily customized to accommodate articles of varying shape and size without changing the design of the base unit.

U.S. Pat. No. 5,256,308 issued to Dully discloses a method for treating paint comprising collecting overspray paint into a sump, adding a stabilizing compound to the water in the sump, adding a paint cure catalyst to accelerate the cure of the paint, assisted by heat and then filtering the cured paint from the clean water filtrate.

U.S. Pat. No. 5,443,738 issued to Bhatnagar discloses a recovery plant for surplus water paint in paint-spraying booths having a circuit of water circulating in the booth wherein such problems with sedimenting water paint particles no longer arise.

U.S. Pat. No. 5,453,301 issued to Saatweber discloses a process for recovering the overspray of aqueous coating agents during spray application by collecting it in an aqueous washing liquid which is continuously circulated in a circuit to the spray booth, where the solids concentration of said washing liquid is maintained within a range.

U.S. Pat. No. 5,569,384 issued to Saatweber discloses a process for recovering the overspray of aqueous coating agents during spray application in spray booths in which aqueous circulating liquid is circulated for the purpose of collecting overspray.

U.S. Pat. No. 5,607,498 issued to Reighard discloses a system and method for controlling air flow through the interior of a powder spray booth includes a powder collection system for collecting oversprayed powder from the interior of the spray booth. The powder collection system includes a powder collector with a powder collection chamber, a pulse plenum chamber, and a fan plenum chamber containing a motor driven fan for drawing the air-entrained powder into the fan plenum chamber so that the oversprayed powder is collected on the cartridge filters and filtered air is exhausted from the fan plenum chamber through one or more final filters.

U.S. Pat. No. 6,468,508 issued to Laughlin discloses a system for coating human skin, a chemical composition, such as a cosmetic or medical formulation, is uniformly coated over the entire body or selected parts of the body of the person being coated.

These previously issued U.S. patents show several different overspray collection type booths, but are not suitable for the use in providing a low cost, simplified collection device. Therefore, there is a need for an Overspray Collection Booth as shown and claimed here.

SUMMARY OF THE INVENTION

A primary objective of the claimed invention is to provide an Overspray Collection Booth that is specifically designed for the collection of tanning fluid during the airbrush application of tanning fluid to a person.

A further objective of the claimed invention is to provide an Overspray Collection Booth that is lower in cost.

An even further objective of the claimed invention is to provide an Overspray Collection Booth that occupies a minimum amount of floor space.

A still further objective of the claimed invention is to provide an Overspray Collection Booth that is easy to operate.

To achieve these objectives, as well as others that will become apparent after reading this specification and view the appended drawings, an Overspray Collection Booth is provided. The Overspray Collection Booth generally comprises a booth having a plurality of vent apertures and an overspray collection system connected to the vent apertures. The Overspray Collection Booth was designed to occupy as little floor space as possible so that the Overspray Collection Booth could be used in a variety of setting where floor space is an important consideration. There are preferably thirteen 1½ inch diameter vent apertures arranged in five zones within the first side wall and second side wall of the booth to collect tanning fluid overspray during the application of tanning fluid to a person standing in the Overspray Collection Booth.

The overspray collection system comprises an upper venting conduit line, a middle venting conduit line, a lower venting conduit line, a common collection line and a suction means. The venting conduit lines and the common collection line are preferably made of polyvinyl chloride plastic to reduce the overall cost and weight of the Overspray Collection Booth. An air flow control valve is included in the vent connections nearest the common collection line so that a technician using the Overspray Collection Booth can control suction rates to each of the vent apertures to achieve a desirable result. The common collection line has threaded end cap at each end with bottom end cap serving as a clean out point for any liquid draining from the venting conduit lines. The suction means has a plastic conduit suction line connected to the common collection line and to a motorized electric fan. A collection receptacle partially filled with water is placed below the output of the motorized electric fan to catch airborne particles sucked from the booth through the collection system.

A customer desiring application of tanning fluid to their body stands inside the Overspray Collection Booth with the collection system of the Overspray Collection Booth in operation. A technician standing outside of the Overspray Collection Booth uses a compressed air airbrush to apply tanning fluid to the person desiring an application of the tanning fluid. The collection system creates a suction action within the booth that draws any airborne tanning fluid that may ricochet off of the customer through the vent apertures and into the collection system. The suction action within the booth creates a relative low pressure area within the booth with respect to the ambient air pressure within the room where the booth is located. The pressure difference draws air through the booth opening from outside of the booth providing fresh air for the customer and technician as well as accelerating the drying time of the tanning fluid on the customer. An alternative embodiment of the Overspray Collection Booth includes a door with a plurality of fans to increase the air flow rate within the booth, thus significantly decreasing the tanning fluid drying time.

BRIEF DESCRIPTION OF THE DRAWINGS

FIG. 1 shows a front perspective view of the Overspray Collection Booth.

FIG. 2 shows a rear perspective view of the Overspray Collection Booth.

FIG. 3 shows a two dimensional view of the first side of the Overspray Collection Booth.

FIG. 4 shows a rear two dimensional view of the second side of the Overspray Collection Booth.

FIG. 5 shows a rear two dimensional view of the rear of the Overspray Collection Booth.

FIG. 6 illustrates how the Overspray Collection Booth is used.

FIG. 7 illustrates how the Overspray Collection Booth operates.

FIG. 8 shows an alternate embodiment of the Overspray Collection Booth.

DETAILED DESCRIPTION OF THE PREFERRED EMBODIMENT

Figure 1:
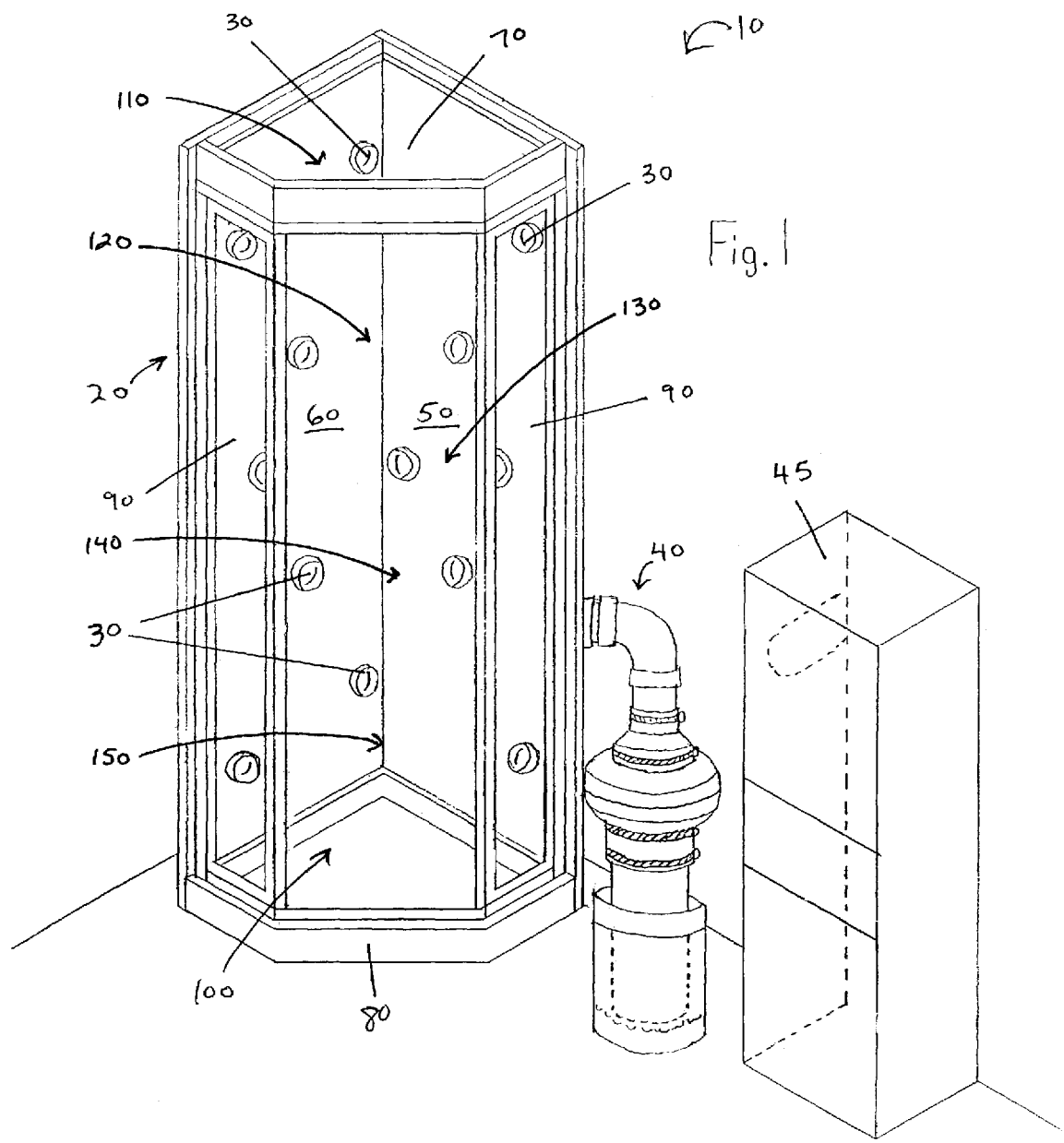
FIG. 1.
Figure 2:
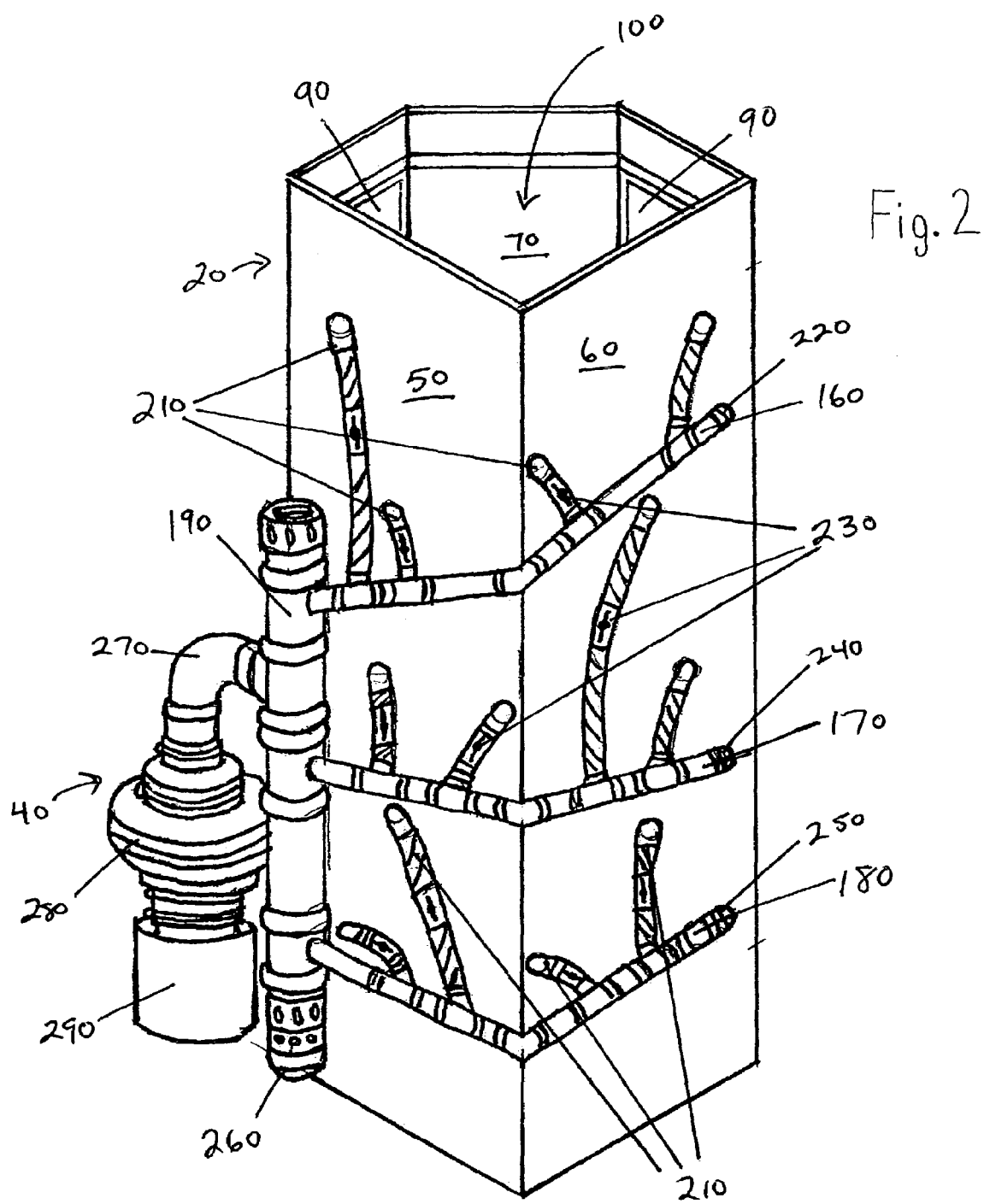
FIG. 2.
Figure 3:
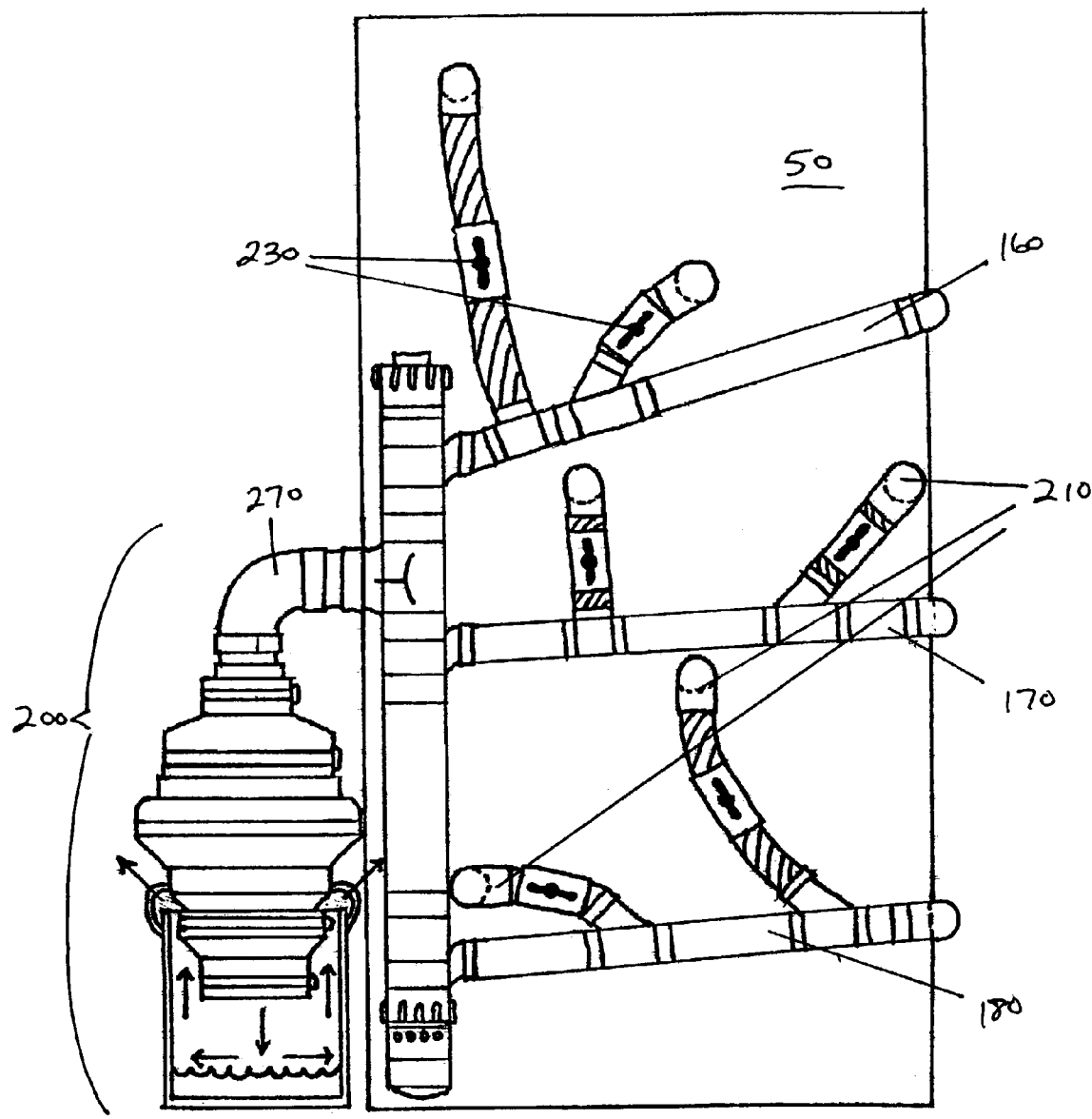
FIG. 3.
Figure 4:
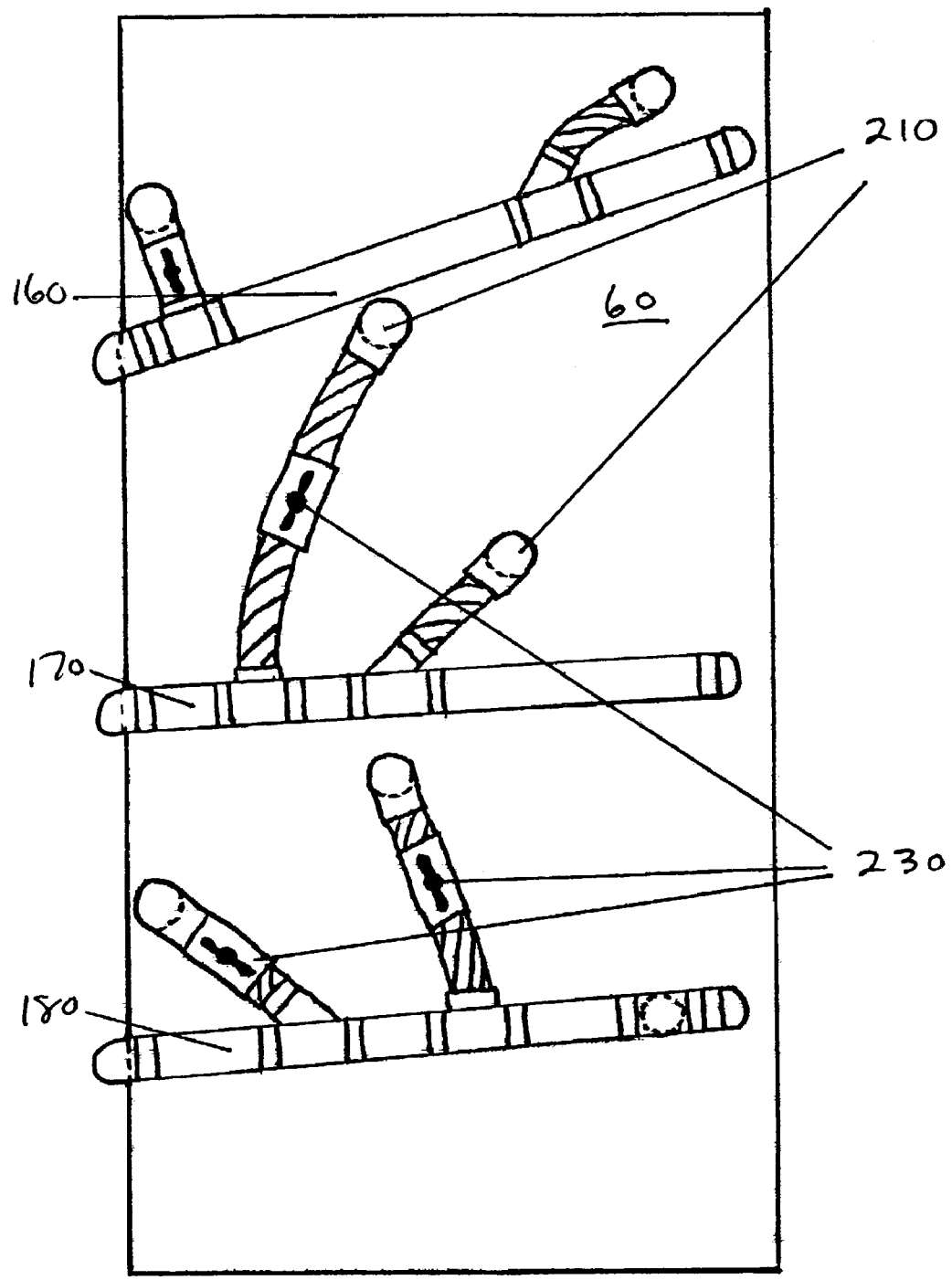
FIG. 4.

Turning now to the drawings, the preferred embodiment of the Overspray Collection Booth 10 as shown in FIGS. 1 and 2 generally comprises a booth 20 having a plurality of vent apertures 30 and an overspray collection system 40 connected to the vent apertures 30 optionally having a collection system cover 45. As will be explained in detail, the Overspray Collection Booth 10 shown and described in this preferred embodiment is especially designed to collect tanning fluid overspray during the application of tanning fluid to a person by a technician using a manually operated compressed air type air brush device.

This preferred embodiment of the Overspray Collection Booth 10 was designed to occupy as little floor space as possible so that the Overspray Collection Booth 10 could be used in a variety of setting where floor space is an important consideration, such as beauty salons, tanning shops, and health clubs. However, it should be noted that the Overspray Collection Booth 10 can be used in a variety of similar applications where water soluble fluids are spayed upon a person such as medicinal solutions being applied to burn victims.

The preferred embodiment of the booth 20 as shown in FIGS. 1 and 2 comprises a first side wall 50, a second side wall 60, a top 70, a bottom 80, two front panels 90 forming a booth opening 100, and a plurality of vent apertures 30. The first side wall 50 and the second side wall 60 are each 78 inches in height and 38 inches in width including the height of the bottom 80 and top 70 of the booth 20. The first side wall 50, second side wall 60, bottom 80 can be constructed of several different suitable such as plywood or metal, but is preferably made of opaque polyurethane plastic to reduce the overall weight of the booth 20. The top 80 is preferably made of a transparent material such as glass or transparent plastic to allow light to enter the booth 20. The overall dimensions of each of the front panels 90 are 78 inches in height and 20 inches in width, making the booth opening 100 25¼ inches in width. The two front panels 90 are preferably made of glass or a transparent plastic but may also be made of the same material used to create the first and second side walls. The booth 20 has a neo-angle design so that the booth 20 can be placed in a corner of a room to reduce the amount of floor space occupied by the booth 20. However, the shape and design of the booth 20 could be constructed in several different configurations and still provide effective overspray collection of airborne particles in the booth 20.

There are preferably thirteen 1½ inch diameter vent apertures 30 arranged in five zones within the first side wall 50 and second side wall 60 of the booth 20 to collect tanning fluid overspray during the application of tanning fluid to a person standing in the Overspray Collection Booth 10. However, the size and placement of the vent apertures 30 could vary and still achieve the objectives of the claimed invention. FIGS. 1–5 show the placement of the vent apertures 30 in the booth 20.

Figure 8:
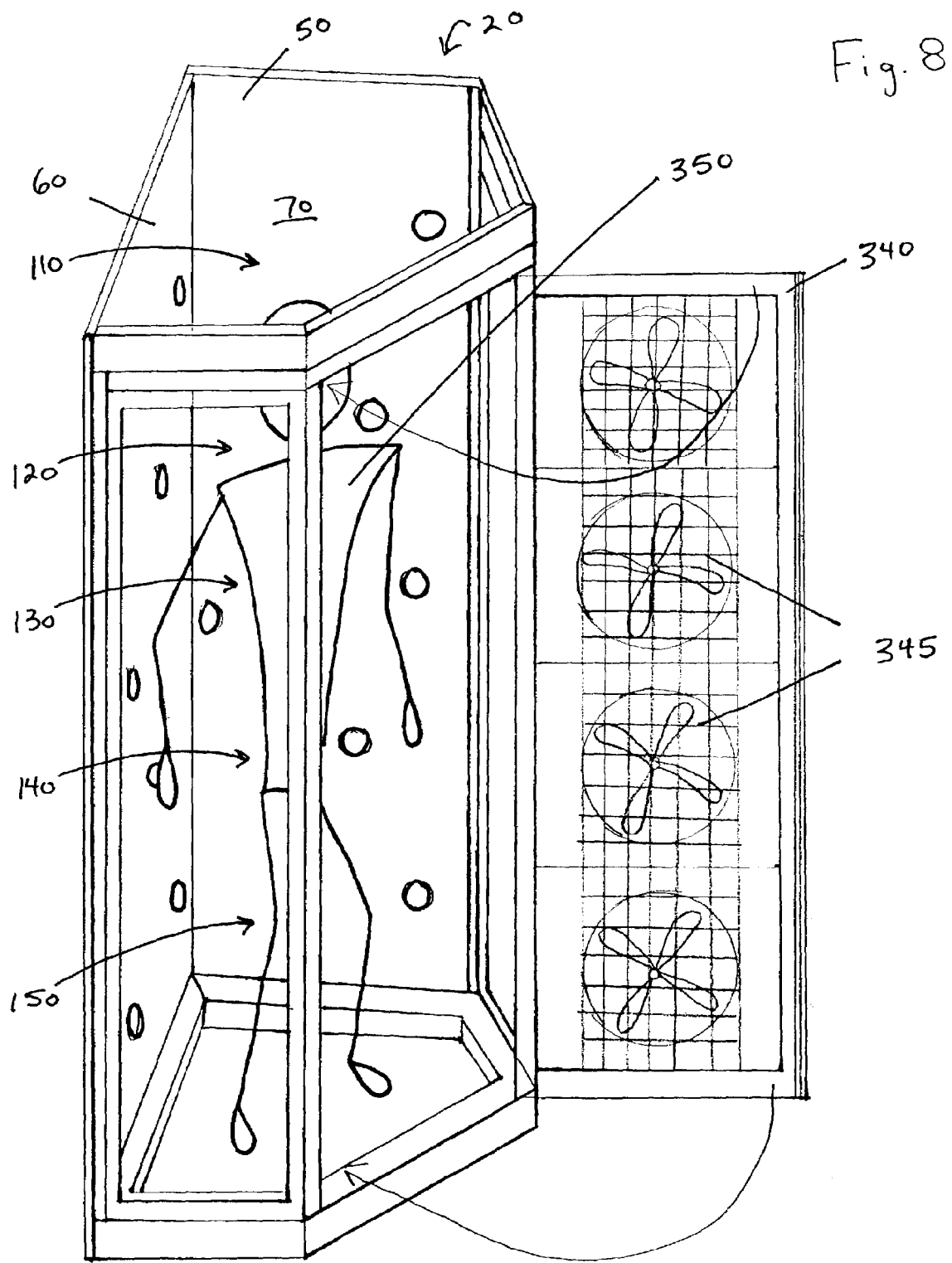
FIG. 8.

FIGS. 1 and 8 show the first zone of vent apertures 110 preferably has three vent apertures 30 placed within the upper 15 inches of the first and second side walls 50, 60 of the booth 20, with the first side wall 50 having one vent aperture 30 and the second side wall 60 having two vent apertures 30. The second zone of vent apertures 120 preferably has two vent apertures 30 placed from 15 inches to 30 inches from the top of the first and second side walls 50, 60, with each of the first and second side walls 50, 60 having one vent aperture 30. The third zone of vent apertures 130 preferably has three vent apertures 30 place from 30 inches to 45 inches from the top of the first and second side walls 50, 60, with the first side wall 50 having two vent apertures 30 and the second side wall 60 having one vent aperture 30. The fourth zone of vent apertures 140 preferably has three vent apertures 30 placed from about 45 inches to about 60 inches from the top of the first and second side walls 50, 60, with the first side wall 50 having one vent aperture 30 and the second side wall 60 having two vent apertures 30. The fifth zone of vent apertures 150 preferably has two vent apertures 30 placed within the lower 18 inches of the first and second side walls 50, 60, with each of the first and second side walls 50, 60 having one vent aperture 30.

The preferred embodiment of the overspray collection system 40 as shown in FIGS. 1 and 2 comprises an upper venting conduit line 160, a middle venting conduit line 170, a lower venting conduit line 180, a common collection line 190 and a suction means 200. The venting conduit lines 160, 170, 180 and the common collection line 190 are preferably made of polyvinyl chloride plastic to reduce the overall cost and weight of the Overspray Collection Booth 10, but may be made of other suitable materials to accomplished the desired objectives of the claimed invention. Each of the venting conduit lines are angled downwardly toward the common collection line 190 so that the connection between the venting conduit lines 160, 170, 180 and the common collection line 190 is the lowest point in a venting conduit line.

Figure 5:
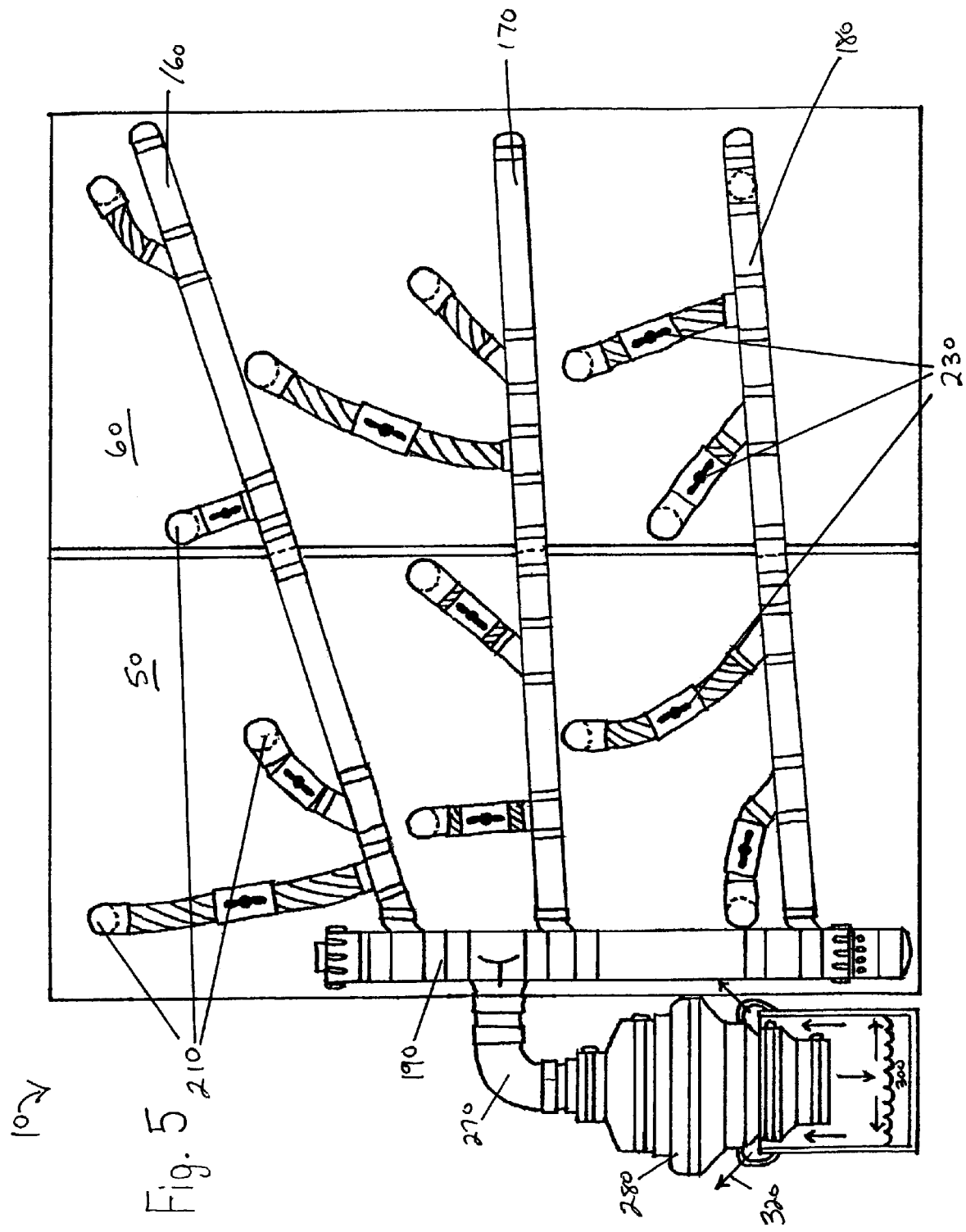
FIG. 5.

FIGS. 2–5 shows the upper venting conduit line 160 has four venting connections 210 connecting the vent apertures 30 of the first and second zones 110, 120 to the upper venting conduit line 160. The upper venting conduit line 160 is made of 2 inch diameter polyvinyl chloride plastic conduit with a threaded end cap 220 and has a 90 degree angle bend between the second and third vent apertures 30 to conform to the 90 degree angle orientation of the first side wall 50 with respect to the second side wall 60. FIG. 5 shows that the first three of the venting connections 210 connected to the upper venting conduit line 160 have a ball valve 230 that enables a technician using the Overspray Collection Booth 10 to control the air flow suction rates to each of the vent apertures 30 connected to the upper venting conduit line 160 to achieve a desirable result.

FIGS. 2–5 show the middle venting conduit line 170 has four venting connections 210 connecting the vent apertures 30 of the second and third zones 120, 130 to the middle venting conduit line 170. The middle venting conduit line 170 is made of 2 inch diameter polyvinyl chloride plastic conduit with a threaded end cap 240 and has a 90 degree angle bend between the second and third vent aperture 30 to conform to the 90 degree angle orientation of the first side wall 50 with respect to the second side wall 60. FIG. 5 shows that the first three of the venting connections 210 connected to the middle venting conduit line 170 have a ball valve 230 that enables a technician using the Overspray Collection Booth 10 to control the suction rates to each of the vent apertures 30 connected to the middle venting conduit line 170 to achieve a desirable result.

FIGS. 2–5 show the lower venting conduit line 180 has five venting connections 210 connecting the vent apertures 30 of the fourth and fifth zones 140, 150 to the lower venting conduit line 180. The lower venting conduit line 180 is made of 2 inch diameter polyvinyl chloride plastic conduit with a threaded end cap 250 and has a 90 degree angle bend between the second and third vent aperture 30 to conform to the 90 degree angle orientation of the first side wall 50 with respect to the second side wall 60. FIG. 5 shows that the first four of the venting connections 210 connected to the lower venting conduit line 180 have a ball valve 230 that enables a technician using the Overspray Collection Booth 10 to control the suction rates to each of the vent apertures 30 connected to the lower venting conduit line 180 to achieve a desirable result.

The common collection line 190 is made of 3 inch diameter polyvinyl chloride plastic conduit with a threaded end cap at each end. The bottom end cap 260 serves as a clean out point for any liquid draining from the venting conduit lines 160, 170, 180. The suction means 200 is preferably connected to the common collection line 190 above the connection between the middle venting conduit line 170 and common collection line 190 and below the connection between the upper venting conduit line 160 and the common collection line 190. However, the suction means 200 may be connected to the venting conduit lines in various different configurations and still achieve the objectives of the claimed invention.

The suction means 200 has a 3 inch polyvinyl chloride plastic conduit suction line 270 connected to the common collection line 190 and to a motorized electric fan 280. Preferably, a Model 150, 160, 200 or 225 electric fan made by Fantech, Inc. currently located at 1712 Northgate Boulevard, Sarasota, Fla. 34234 is used to create the suction in the collection system 40. However, the type and brand of suction means 200 can be of several different types of make and manufacture so long as the suction means 200 can create a flow rate of from about 250 cubic feet per minute (cfm) to about 450 cfm in a setting where the static pressure is zero. During the development of the Overspray Collection Booth 10, several different configurations and sizes of fans 280, venting conduit lines 160, 170, 180 and vent apertures 30 were tested to arrive at the preferred embodiment of the claimed invention. It was discovered through testing that the use of 1½ inch vent apertures 30, 2 inch venting conduit lines 160, 170, 180 and a 250 cfm to 450 cfm fan 280 yielded the best results.

Figure 6:
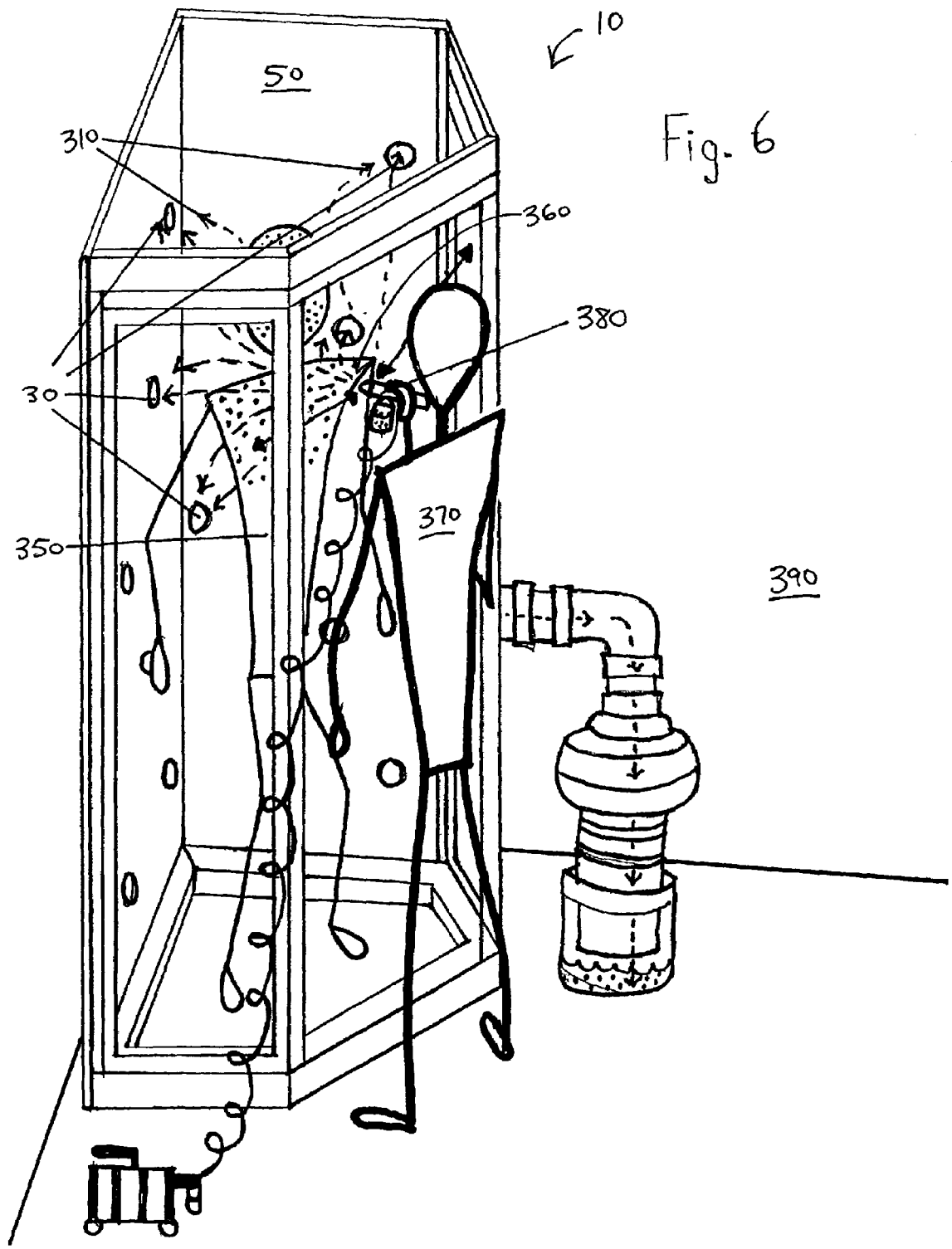
FIG. 6.
Figure 7:
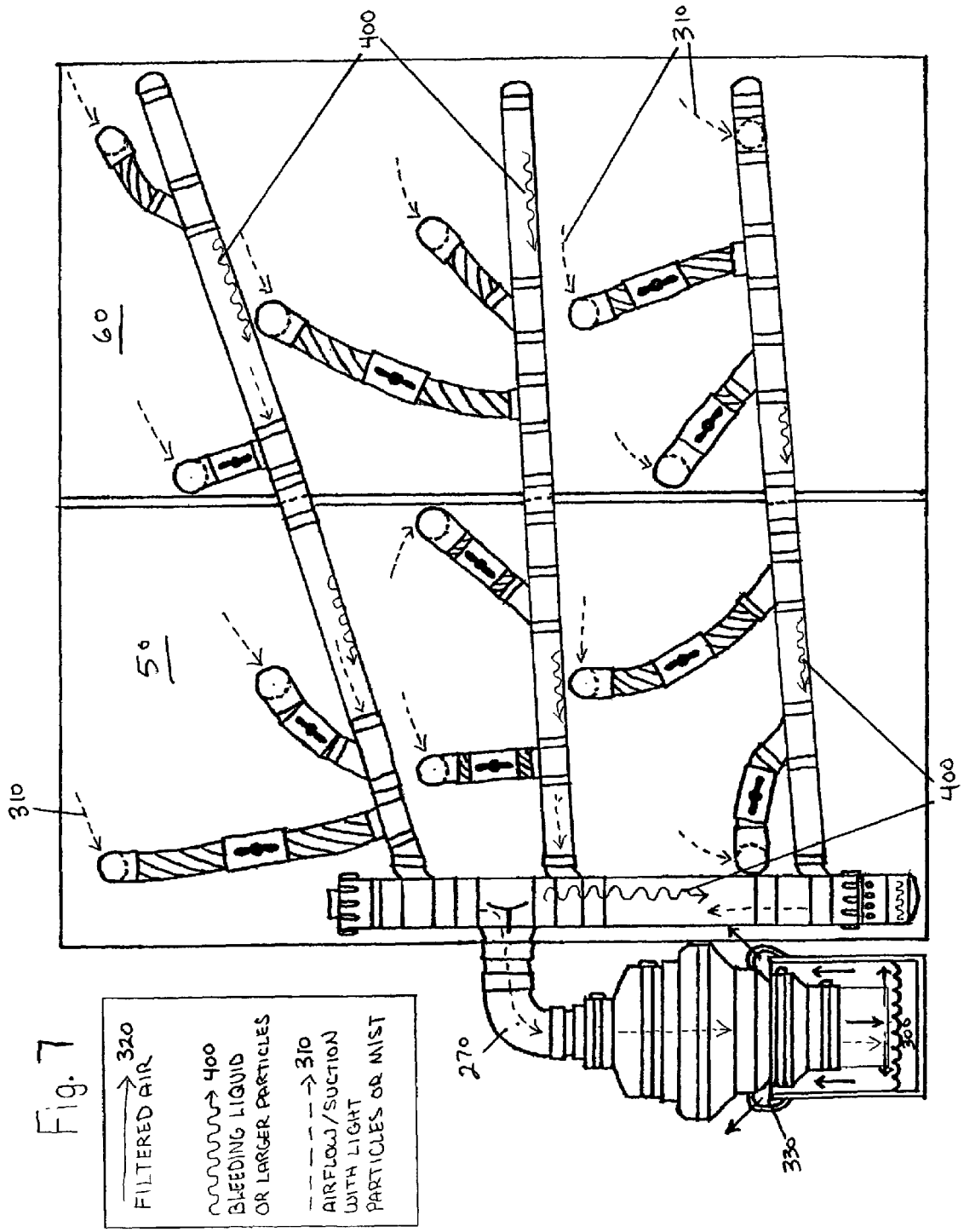
FIG. 7.

FIGS. 5–7 show a collection receptacle 290 partially filled with water 300 is placed below the output of the motorized electric fan 280 to catch airborne particles 310 sucked from the booth 20 through the collection system 40. The tanning fluid commonly used in these type of airbrush tanning applications are typically water soluble. When the airborne tanning fluid particles 310 captured by the collection system 40 are pushed out of the fan 280 and into the water 300 within the collection receptacle 290, the water 300 captures the tanning fluid particles 310 and dissolves them, thus filtering the air. The filtered air 320 is then allowed to escape from the collection receptacle 290 through an opening 330 provided at the top of the collection receptacle 290.

FIG. 8 show an alternative embodiment of the Overspray Collection Booth 10 where the booth opening 100 has a door 340 equipped with a plurality of drying fan 345. The door 340 is sized and shaped to fill the booth opening 100 so that the customer 350 inside the booth 20 is totally enclosed within the booth 20. The air flow combination of the drying fans 345 with the suction action of the collection system 40 significantly decreases the drying time of the tanning fluid on the customer's body resulting in a quicker cycle time for performing the tanning service and thus increasing the number of customers that may be served within a given time period.

The Overspray Collection Booth 10 is used as illustrated in FIG. 6. A customer 350 desiring application of tanning fluid 360 to their body stands inside the Overspray Collection Booth 10 with the collection system 40 of the Overspray Collection Booth 10 in operation. A technician 370 standing outside of the Overspray Collection Booth 10 uses a compressed air airbrush 380 to apply tanning fluid 360 to the customer 350. The collection system 40 creates a suction action within the booth 20 that draws any airborne tanning fluid 310 that may ricochet off of the customer 350 through the vent apertures 30 and into the collection system 40. The suction action within the booth 20 creates a relative low pressure area within the booth 20 with respect to the ambient air pressure within the room 390 where the booth 20 is located. The pressure difference draws air through the booth opening 100 from outside of the booth 20 providing fresh air for the customer 350 and technician 370 as well as accelerating the drying time of the tanning fluid on the customer 350.

FIG. 7 shows how the collection system 40 operates. Airborne particles of tanning fluid 310 are sucked from the booth 20 through the collection system 40 and into the suction means 200. The output of the suction means 200 pushes the airborne particles of tanning fluid 310 into the collection receptacle 290 where the tanning fluid dissolves in water 300. Larger particles of tanning fluid and bleeding tanning fluid liquid 400 that gathers on the interior walls of the venting conduit lines 160, 170, 180 flow downwardly with the slope of the venting conduit lines 160, 170, 180 and fall into the common collection line 190. The suction line 270 is connected to the common collection line 190 between the upper venting conduit line 160 and the middle venting conduit line 170 so that a minimum amount of liquefied tanning fluid 400 will be drawn from the venting conduit lines 160, 170, 180 into the suction means 200. Preferably, the slope of the upper venting conduit line 160 is greater than the slope of the middle venting conduit line 170 and the lower venting conduit line 180 so that the pull of gravity increases the velocity of the liquefied tanning fluid 400 to further aid in preventing liquefied tanning fluid 400 from being drawn in the suction means 200 from the upper venting conduit line 160.

Although the invention has been described by reference to some embodiments it is not intended that the novel device be limited thereby, but that modifications thereof are intended to be included as falling within the broad scope and spirit of the foregoing disclosure, the following claims and the appended drawings.

I claim:

1. A booth for the collection of tanning fluid overspray, the booth comprising:
    a booth sized and shaped to enclose a person having a first side wall and a second side wall, the booth having an open portion sized and shaped for ingress and egress by a person;
    a plurality of vent apertures within the first side wall and the second side wall, the vent apertures being vertically spaced within the first side wall and the second side wall corresponding to a plurality of vertically spaced anatomical zones of a user's body to provide effective collection of airborne particles adjacent each vertically spaced anatomical zone;
    a plurality of venting conduit lines having a plurality of venting connections connected to the vent apertures;
    a common collection line collected to each of the plurality of venting conduit lines;
    suction means connected to the common collection line providing suction within the venting conduit lines, the suction drawing airborne particles within the booth through the vent apertures, venting connections and the venting conduit lines; and
    collection means adjacent to the suction means, the suction means drawing the airborne parties within the venting conduit lines into the collection means.

2. The booth of claim 1 wherein the venting conduit lines are angled downwardly toward the common collection line to provide a draining means for liquid gathering on interior walls of the venting conduit lines, the liquid gathering on the interior walls of the venting conduit lines draining into the common collection lines.

3. The booth of claim 2 wherein the suction means is connected to the common collection line at a point where gravity minimizes the amount of liquid being drawn into the suction means from the common collection line.

4. The booth of claim 3 further comprising a door sized and shaped to cover the open portion of the booth, the door having at least one air movement means increasing the air flow through the booth.

5. The booth of claim 4 further comprising a clean out point below the venting conduit line connections to the common collection line.

6. The booth of claim 5 further comprising at least one air flow control valve within the plurality of plurality of venting conduit lines.

7. The booth of claim 6 wherein the suction means is a motorized fan enclosed within a housing.

8. The booth of claim 7 wherein the collection means further comprises a dissolution means for dissolving dissolvable airborne particles.

9. An airborne matter collection booth assembly, the airborne matter collection booth assembly for collecting airborne matter adjacent a user's body, the airborne matter collection booth assembly comprising:
    a booth sized and shaped to enclose a user, the booth comprising at least two side walls and an ingress-egress portion, the ingress-egress portion extending intermediate the two side walls, the ingress-egress portion for enabling the user's body to enter-exit the booth;
    a plurality of vent apertures, the vent apertures being vertically spaced and extending through the side walls, the vent apertures corresponding to a plurality of vertically spaced anatomical zones of the user's body, the vent apertures enabling effective collection of airborne matter adjacent each vertically spaced anatomical zone;
    a plurality of venting conduit lines, the venting conduit lines being cooperatively associated with the vent apertures;
    suction means, the suction means being cooperatively associated with the venting conduit lines for providing suction within the venting conduit lines, the suction directing the airborne matter through the vent apertures and the venting conduit lines; and
    collection means, the collection means being cooperatively associated with the suction means, the suction means directing the airborne matter from the venting conduit lines into the collection means.

10. The booth assembly of claim 9 wherein the airborne matter comprises liquid particles and the venting conduit lines are angled downwardly toward the collection means, the downwardly angled venting conduit lines providing drain means, the drain means for directing liquid gathering on interior walls of the venting conduit lines into the collection means.

11. The booth assembly of claim 9 further comprising a door sized and shaped to cover the ingress-egress portion, the door comprising air movement means, the air movement means for increasing airflow through the booth.

12. The booth assembly of claim 9 wherein at least one venting conduit line comprises airflow control means.

13. The booth assembly of claim 9 wherein the collection means comprises dissolution means, the dissolution means for dissolving dissolvable airborne matter.

14. A booth for collecting airborne matter adjacent a user, the booth comprising:
    at least two side walls and an ingress-egress portion, the ingress-egress portion extending intermediate the two side walls, the side walls being sized and shaped to surroundingly receive the user, the ingress-egress portion enabling the user to pass intermediate the side walls;
    a plurality of vent apertures, the vent apertures being vertically spaced and extending through the side walls, the vent apertures corresponding to a plurality of vertically spaced anatomical zones, the vent apertures enabling collection of airborne matter adjacent each vertically spaced anatomical zone;
    suction means, the suction means being cooperatively, associated with the vent apertures for providing suction adjacent thereto, the suction directing the airborne matter through the vent apertures; and collection means, the collection means being cooperatively associated with the suction means, the suction means directing the airborne matter from the vent apertures into the collection means.

15. The booth of claim 14 wherein the suction means comprise a plurality of venting conduit lines, the venting conduit lines extending intermediate the vent apertures and the collection means.

16. The booth of claim 15 wherein the airborne matter comprises liquid particles and the venting conduit lines are angled downwardly toward the collection means, the downwardly angled venting conduit lines providing drain means, the drain means for directing liquid gathering on interior walls of the venting conduit lines into the collection means.

17. The booth of claim 14 further comprising a door sized and shaped to cover the ingress-egress portion, the door comprising air movement means, the air movement means for increasing airflow through the booth.

18. The booth of claim 16 wherein at least one venting conduit line comprises airflow control means.

19. The booth of claim 14 wherein the collection means comprises dissolution means, the dissolution means for dissolving dissolvable airborne matter.

* * * * *